United States Patent [19]
Grimm et al.

[11] Patent Number: 6,083,200
[45] Date of Patent: Jul. 4, 2000

[54] MEDICAL SYRINGE

[76] Inventors: Edgardo Grimm, Rue Champréveyres 1, 2000 Neuchâtel; Olinto Moro, Avenue d'Ouchy 39, 1006 Lausanne, both of Switzerland

[21] Appl. No.: 09/308,794
[22] PCT Filed: Oct. 28, 1997
[86] PCT No.: PCT/CH97/00410
  § 371 Date: Mar. 25, 1999
  § 102(e) Date: Mar. 25, 1999
[87] PCT Pub. No.: WO98/23316
  PCT Pub. Date: Jun. 4, 1998

[30] Foreign Application Priority Data

Nov. 27, 1996 [CH] Switzerland .............................. 2922/96

[51] Int. Cl.⁷ .................................................. A61M 5/00
[52] U.S. Cl. ........................................... 604/110; 604/218
[58] Field of Search ..................... 604/110, 218, 604/228, 187, 238

[56] References Cited

U.S. PATENT DOCUMENTS 5,026,346 6/1991 Bates ........................................ 604/110
5,078,686 1/1992 Spanner et al. ........................ 604/110
5,226,881 7/1993 Pickhard ................................. 604/110
5,944,692 8/1999 McGary et al. .................... 604/218 X

FOREIGN PATENT DOCUMENTS 0345159 12/1989 European Pat. Off. .
2298340 8/1976 France .
2606643 5/1988 France .
2207054 1/1989 United Kingdom .
WO 9003817 4/1990 WIPO .

*Primary Examiner*—John D. Yasko
*Attorney, Agent, or Firm*—Clifford W. Browning; Woodard, Emhardt, Naughton, Moriarty & McNett

[57] ABSTRACT

The invention concerns a medical syringe comprising a tubular body, in which slides a plunger comprising an opening, the plunger comprising a sealing piece, movable in the plunger and which closes the opening of the syringe before it is used. The assembly is arranged such that, after the syringe has been used, the sealing piece no longer closes the opening permanently, so that the syringe cannot be used again. All the parts of the syringe are designed for being produced by moulding and automatically mounted in series by axial jointing.

10 Claims, 4 Drawing Sheets

MEDICAL SYRINGE

The present invention relates to a medical syringe made up of elements allowing one injection but preventing the use of the same syringe for any subsequent injection. In brief, this is a non-reusable syringe, which self-destructs without special manipulation by the operator.

Naturally, for obvious reasons, hospital and medical environments have for a long time been using disposable syringes which are used once only. However these environments are not the only ones to use syringes and trusting the user's self-discipline alone to ensure once-only use is far from adequate in the real world. For example it is well-known, according to WHO studies, that in developing countries so-called disposable syringes are often re-used up to 50 times.

That is why numerous proposals have been made to make syringes which, through-the way in which they are designed or constructed, physically prevent their being used a second time.

The choice of the means to be adopted to this end is very limited. In fact there is really only one way, namely fitting the chamber of the syringe, basically the head of the piston, with a provisional blocking unit which ensures that the chamber is sealed for the first injection but which is definitively de-activated once the first injection has been made.

The simplest version of this design is described in patent application FR-A-2, 606, 643, relating to a syringe with an eccentric nozzle, where the head of the piston is equipped with an orifice, initially stopped with a moveable cork which is ejected from the chamber when it encounters a centre punch when the piston reaches the end of its path and the chamber reaches its minimum volume.

More sophisticated proposals have also been made, in particular using a membrane held by the piston, which is then either displaced by the pressure of the liquid or punctured at the end of the first injection. Such proposals are to be found in European Patent 0345159 and in Patent application FR-A-2, 606, 643.

The number and variety of proposals of the prior art might suggest that the problem has been fully dealt with. However this is not so. In fact it is not sufficient to design a syringe which can function on this principle or one of the many variants thereof, it then has to be produced by an industrial process which entails a very low cost. In this respect it should be remembered that the industrial manufacture of syringes has to meet two requirements: first of all the quantities are truly astronomical and amount to hundreds of thousands of units in order to achieve simply a modest cost in this context. Secondly, the syringes must be packed in high grade sterile packaging, in spite of the enormous manufacturing output. It is no doubt due to the fact that they did not comply with these two conditions that the proposals of the prior art have not led to any significant production, whereas the need is absolutely well-known and absolutely urgent.

It is from this angle that the criticism of the previous proposals should be made, since it is indeed the case that these proposals do not meet the needs which the world is actually experiencing. In order for a non-reusable syringe to truly meet the need, it is necessary for the unit sale price to be at least comparable with that of a conventional disposable syringe, but it is also necessary for it to be equally reliable. It would actually be ridiculous to allow major production initiatives if the physically unique nature of the use were not guaranteed and remained uncertain, as is the case with the proposals of the prior art.

The use of a membrane is disqualified in an industrial context because these have to be plastic articles and therefore their elasticity is an uncontrollable parameter, in particular over a period of time. Therefore one cannot guarantee stable properties and thus one would be exposed either to the impossibility of making the first injection properly or to the uncertainty of preventing the second injection in all cases. For example in the case of the syringe proposed in European patent 0345159, because there is a flexible membrane at the very end of the piston, the activation of the device is commanded by the nature of the pressure exercised on the liquid to be injected. The least drop in pressure may permanently disrupt the ongoing injection.

The use of an ejected cork is also to be ruled out because it is a plastic article inserted in another and therefore one cannot truly claim to be in control of the moment when the two parts will split up. In other words, the cork may well pop out during the injection simply due to the pressure of the liquid, and likewise it may be ejected in the opposite direction when the liquid is sucked into the syringe. In any case nobody can guarantee that it will not pop out and this is a disadvantage.

The aim of the present invention is thus to propose a non-reusable syringe, whose constituent elements, and the properties thereof in combination with one another, allow on the one hand economical and reliable industrial production and, on the other hand, guarantee, through the controllable mechanical properties of the aforesaid elements, that it really can be used only once.

To this end, the present invention relates to a medical syringe comprising a tubular body, in which a piston slides, the piston having an opening, a blocking unit blocking said opening before the syringe is used and this blocking unit arranged so as to cooperate, when the piston reaches the end of its path, with a counter-piece integral with the tubular body of the syringe, so as to expel said blocking unit out of the opening in such a way that after the syringe has been used the blocking unit can definitively no longer stop up the opening, so that the syringe cannot be re-used. The piston is arranged in such a way that an inner chamber is constituted, inside which the blocking unit is housed, the whole being arranged such that a predetermined path is imposed on the blocking unit, without the use of a distorting element, and the blocking unit has a blocking head engaged in the opening and at least one element arranged so as to prevent its returning to its blocking position. The latter element, before the injection, rests against the inner wall of said inner chamber, so as to generate a force of friction which is added to the force exercised on the blocking head by the edge of the opening, such that when the pressure of the liquid is exercised on the blocking head during the injection it is not sufficient to expel the blocking head out of the opening. All the elements of the syringe are designed such that they can be produced by moulding and fitted on an automatic production line using axial fitting.

In one embodiment of the syringe, the back part of the blocking unit comprises at least one fin which will tolerate an elastic deformation and the free end of which is directed towards the bottom of the syringe body and cooperates with the wall of the inner chamber. The wall of the inner chamber is arranged so as to allow the free end of the fin to slide against the wall of the inner chamber when the blocking unit moves inside the chamber after coming to a stop against the counter-piece but so as then to prevent the free end of the fin sliding in the opposite direction.

The inner chamber may comprise a first space whose dimensions are chosen so as to keep the fin folded back along the blocking unit when the head of the blocking unit is blocking the opening, and a second space whose dimensions are chosen so as to allow the fin to be extended when the blocking unit has been moved inside the piston after hitting the counter-piece.

According to one preferred embodiment, the counter-piece comprises at least one unit which projects from the bottom of the tubular body of the syringe.

Other characteristics, aims and advantages of the invention will emerge more clearly in the light of the description of one embodiment of the syringe and the variants, set out below by way of example and illustrated by the drawings appended in which.

Figure 1:
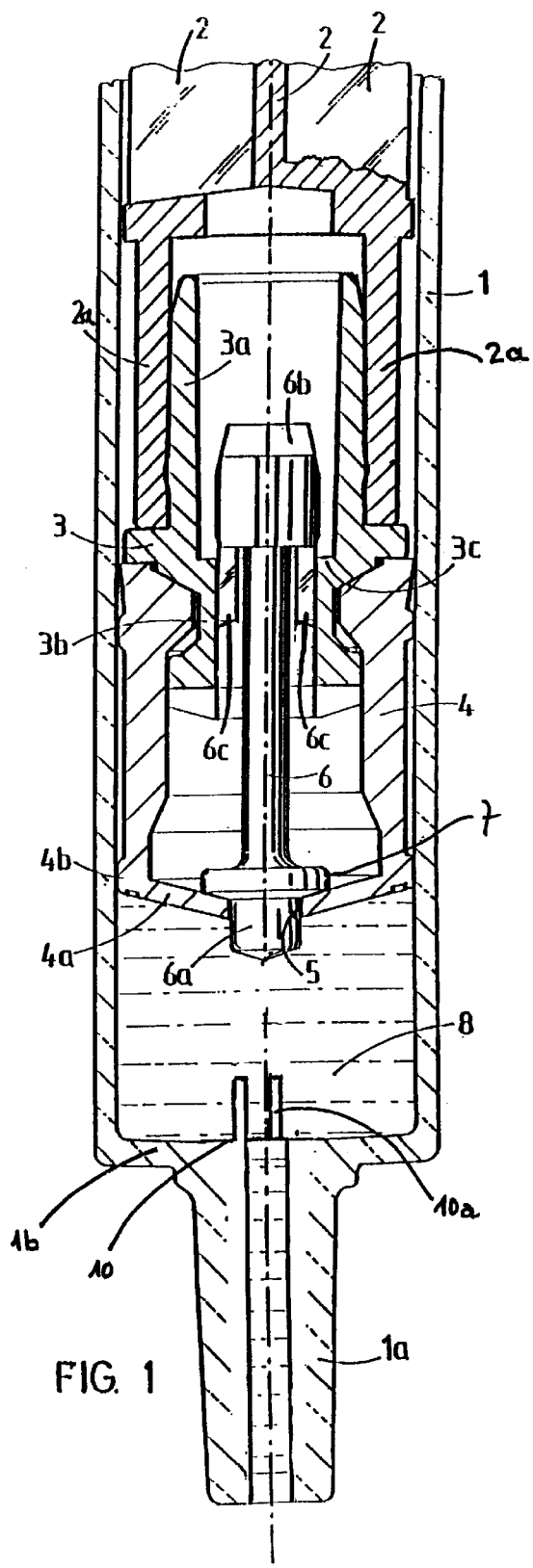
FIG. 1 is an axial section of the front part of a first embodiment of the syringe, as it appears before or during the injection.
Figure 2:
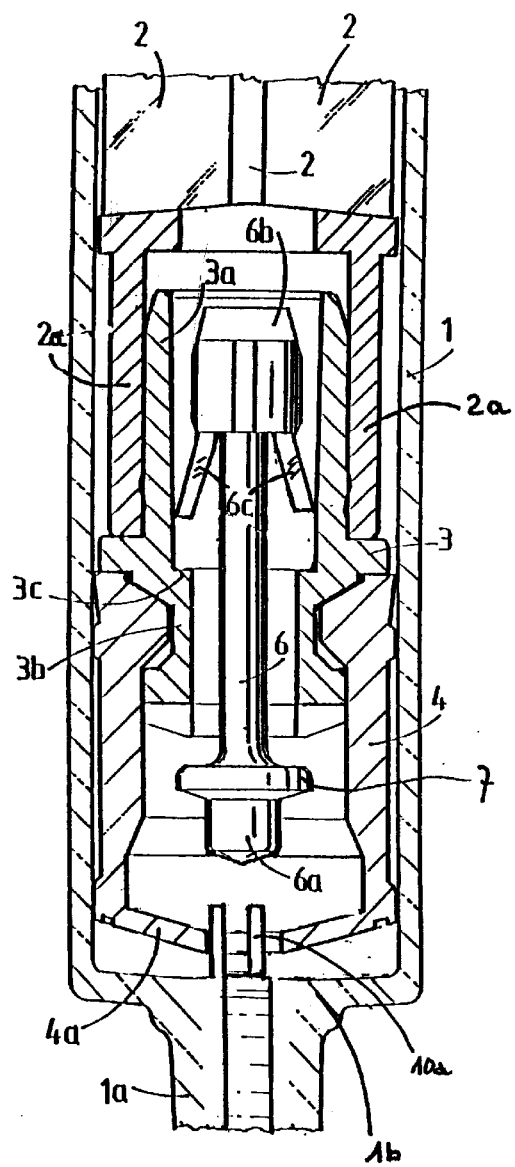
FIG. 2 is a similar section to that of FIG. 1, of the front part of the same syringe, as it appears after an attempt to re-use it.

The syringe shown in FIGS. 1 and 2 comprises a tubular body 1, at the end of which is a nozzle 1a intended to receive a hypodermic needle. A piston activated with the help of a rod 2 slides along in this tubular body. This rod, cross-shaped, ends in an element 2a shaped like a socket.

The piston has an intermediate element 3, of which the top part 3a, in the form of a sleeve, is forced by axial fitting into the element 2a. An element 4, in the shape of a socket, hooks with a notch on to the intermediate element 3. This element 4 has on the one hand an outer bead 4b which is supported against the inner face of the tubular body 1 in order to ensure a seal between the piston and the tubular body and on the other hand a base 4a which is in contact with the liquid 8 to be injected and transmits the thrust of the piston to it.

The piston comprises an inner chamber whose space is bounded by the internal faces of elements 3 and 4 thus linked together. The intermediate element 3 comprises a lower part 3b defining a lower cylindrical space and an adjacent upper part 3a defining an upper cylindrical space, the diameter of the lower cylindrical space being less than that of the upper cylindrical space so as to constitute a shoulder 3c at the junction of the two parts 3a and 3b. Vents have been made within the element 2a in order to adjust the pressure inside the inner chamber to atmospheric pressure.

The base 4a of the element 4 is pierced in the centre by an opening 5 in which the front terminal part 6a is engaged, hereafter called the blocking head 6a of a blocking unit 6. This blocking unit, essentially cylindrical in shape, is housed within the inner chamber of the piston so that its axis of symmetry is superimposed on that of the syringe. The blocking unit is fitted so that it can slide along the walls of the lower part 3a of the intermediate element. It ends, at its rearmost extremity, in a head 6b which has two elastic fins 6c directed towards the front, diametrically opposite one another and held in place before or during a first injection in the position shown in FIG. 1. The dimensions of the blocking head 6a, shaped like a truncated cone, are such that it can settle and slide within the opening 5 whilst ensuring a perfect seal. For example, in the case of a syringe designed to enable the injection of a maximum volume of 2.5 ml of liquid, the opening has a diameter of 2 mm, the truncated cone of the blocking head has a smaller section, whose diameter is equally 2 mm and an upper section whose diameter is 2.5 mm. The blocking head 6a is surmounted by a crown 7 which projects laterally, acting on the one hand as a stop for the positioning of the blocking unit inside the inner chamber and on the other hand helping to seal the aforesaid inner chamber.

The tubular body 1 of the syringe comprises a counter-piece 10 integral with its base 1b, close to the nozzle 1a. This counter-piece comprises lugs 10a which project in relation to the base 1b and which are arranged so that they are located on the extension of the blocking head 6a of the blocking unit, whilst allowing sufficient room for the liquid to be injected. This counter-piece will be explained in detail later.

As can be seen in FIG. 1, the two fins 6c are supported on the walls of the lower part 3a defining the lower cylindrical space. The diameter of this cylindrical space is such that the fins are folded back there, constrained, along the blocking unit.

When the piston is activated, it exercises pressure on the liquid contained in the body which is then ejected through the nozzle 1a.

The forces of friction, exercised both on the fins and on the blocking head 6a of the blocking unit, are such that the pressure which the liquid can exercise on this head is not sufficient to cause the blocking unit 6 to slide.

When the piston reaches the end of its path, the blocking unit 6 comes into contact, via its head 6a, with the lugs 10a of the counter-piece 10 which then acts as a stop. Continuing its path until it reaches the base 1b of the syringe, the piston becomes caught on the counter-piece 10, which drives the blocking head 6a out of the opening 5, then the blocking unit moves inside the inner chamber of the piston, and fins 6c slide along the walls of the lower part 3b of the intermediate element 3, after which the fins are extended inside the upper cylindrical space constituted by the upper part 3a of the intermediate element when their ends pass the shoulder 3c.

The blocking unit is then in the position shown in FIG. 2, the elastic fins 6c are extended in a configuration which renders them more stable and supported on the walls of the upper part 3a, being blocked by the shoulder 3c, thus making it impossible for the blocking unit to return to its initial position, so that the blocking unit definitely no longer blocks the opening 5.

This arrangement means that it is no longer possible to suck up liquid again. In fact, through the release of the opening 5, the inside of the body of the syringe is in communication with the inner chamber of the piston and in turn is adjusted to atmospheric pressure. The piston, through a backward movement, is no longer able to create a negative pressure there.

Figure 3:
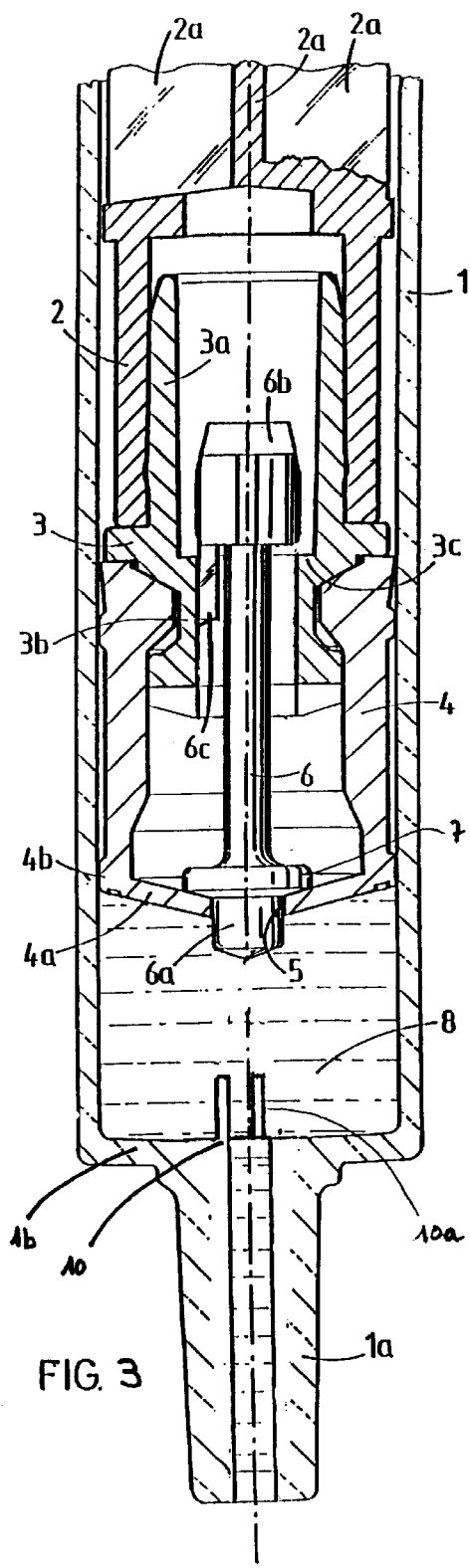
FIG. 3 is an axial section of the front part of a second embodiment of the syringe, as it appears before or during the injection.
Figure 4:
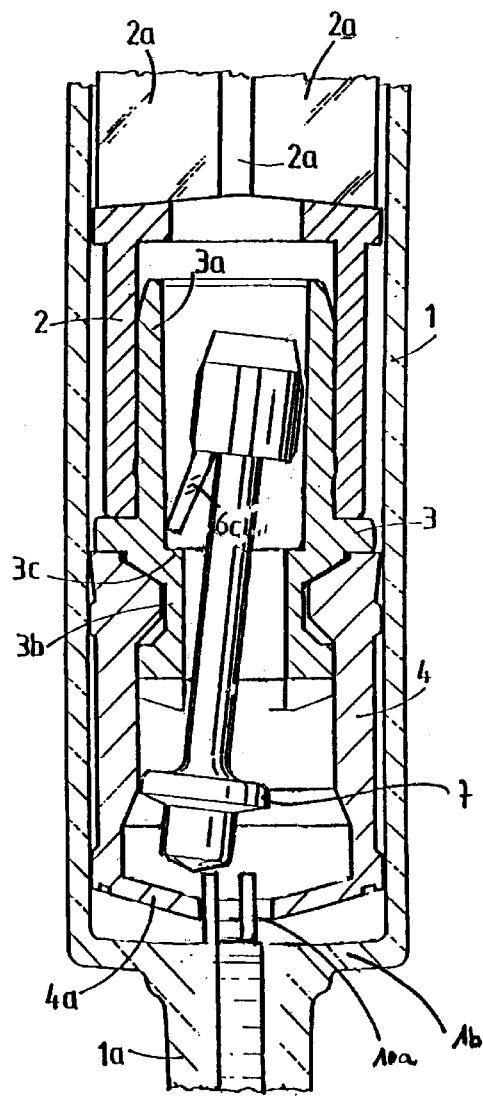
FIG. 4 is a similar section to that of FIG. 3 of the front part of the same syringe, as it appears after an attempt to re-use it.

The variant shown in FIGS. 3 and 4 only differs from the first embodiment in the arrangement of the blocking unit 6. In this variant the blocking unit 6 comprises only one elastic fin 6c, but its structure and function are identical with those of the two fins on the blocking unit if the preceding embodiment.

The presence of this single fin makes the blocking unit asymmetric. Consequently, once the blocking head 6a is forced to move out of the opening 5, the blocking unit 6 pivots on itself under the influence of the thrust of the fin against the wall of the lower part 3b. As FIG. 4 shows the blocking unit then definitively loses its alignment with the opening 5 and is no longer able to block it again.

As FIGS. 1 to 4 show, the counter-piece 10 comprises three lugs 10a which project from the base 1b of the tubular body into the extension of the inner walls of the nozzle 1a. The height of the lugs 10a is chosen so as to cause sufficient displacement of the blocking unit inside the inner chamber of the piston, when the piston reaches the end of its path, as to enable the fins 6c to be deployed inside the upper cylindrical space constituted by the upper part 3a of the intermediate element, as described above.

Figure 5:
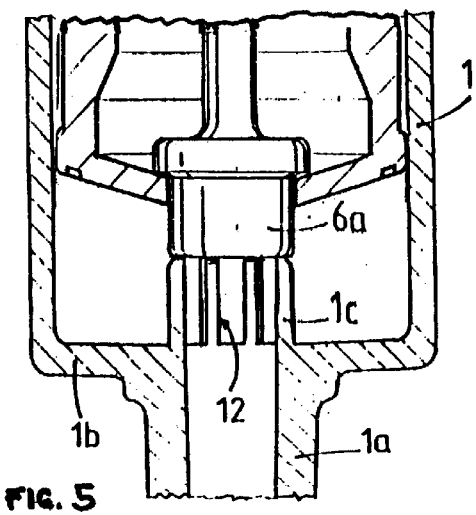
FIGS. 5 to 7 are partial axial sections of the front end of the syringe showing three versions of the counter-piece which acts as a stop for the blocking piece.

According to the variant shown in FIG. 5, the counter-piece 10 is made up of an annular projection 1c provided in the centre of the base 1b of the tubular body of the syringe. This projection 1c is crenellated, which creates passages 12 allowing the liquid contained in the syringe to pass into the nozzle 1a when the blocking head 6a of the blocking unit is supported on the aforesaid projection.

Figure 6:
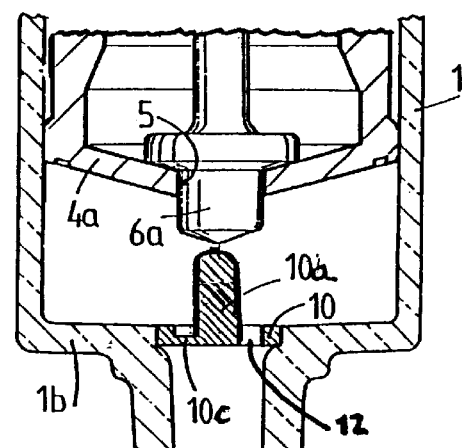

In the variant shown in FIG. 6, the base 1b of the tubular body 1 of the syringe has in the centre a washer 10b with radial arms 10c ending in a central contact point or limit 10a in the form of a lug against which the blocking head 6a stops when the piston reaches the end of its path. The size of this contact point 10a is chosen so as to obtain the effects described above. The washer is inserted in the mass of the syringe body and supported partly on the opening of, the nozzle 1a. The space between the radial arms is sufficient not to obstruct the passage of the liquid to be injected.

Figure 7:
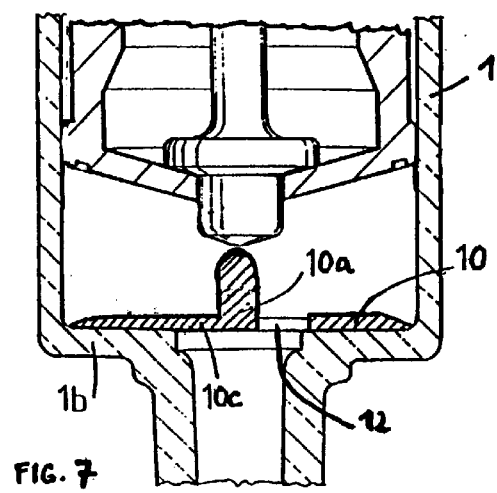

The variant shown in FIG. 7 differs from the preceding variant in the shape of the central washer 10b, placed on the base 1b of the tubular body of the syringe. This washer has radial arms 10c carrying a central contact point 10b against which the blocking head 6a stops when the piston reaches the end of its path. This version offers the advantage that the washer may be arranged on the base of any already existing conventional syringe.

As shown in FIGS. 1 to 4 the element 4 is hooked on by a notch to the intermediate element 3. In order to facilitate assembly, which is carried out by axial fitting, the element 4 is preferably made of a semi-rigid or flexible plastic material, for example synthetic rubber.

Figure 8:
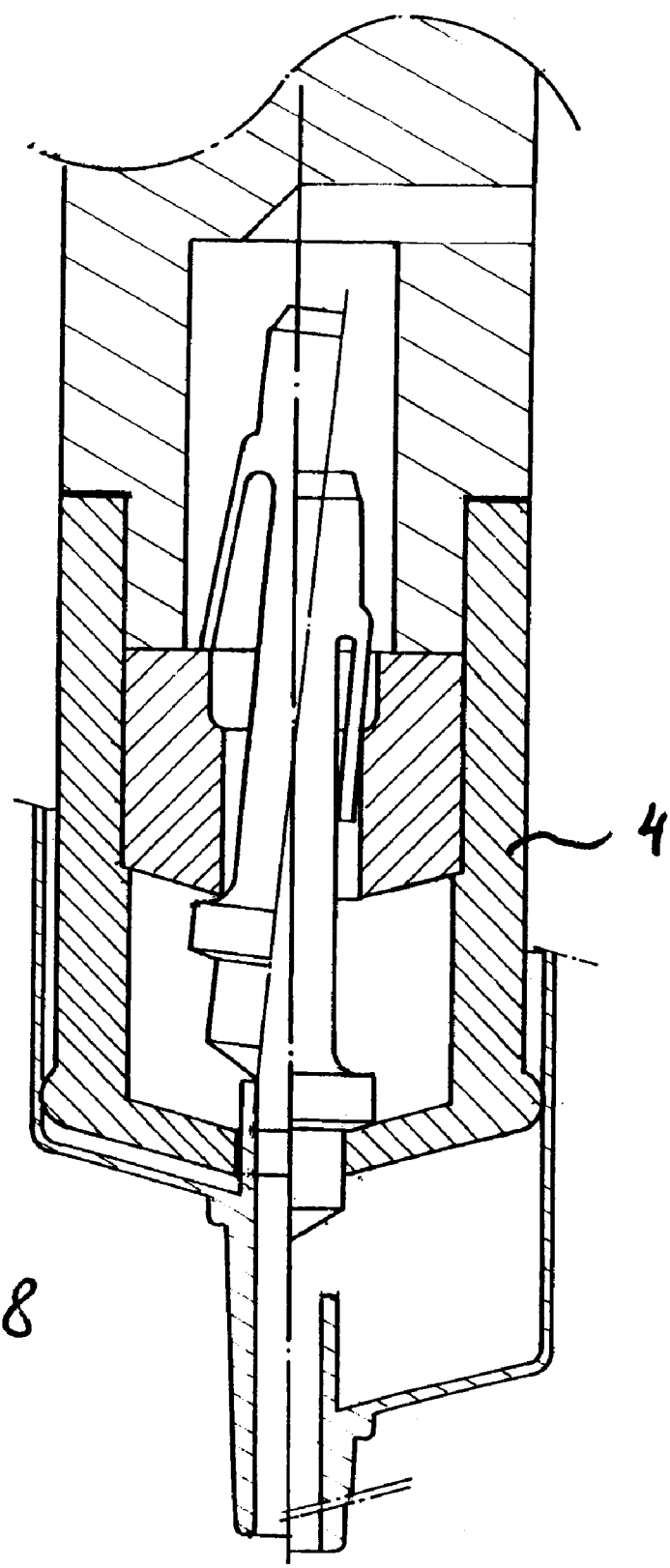
FIG. 8 is an axial section of the front part of a variant embodiment of the syringe, the half-section on the right represents the syringe before the injection and the half-section on the left represents the syringe after the injection.

In one variant embodiment, shown in FIG. 8, the element 4 is made of a rigid plastic material.

The assembly described and shown is easy to manufacture, since all the elements can be simply moulded from plastic and easily assembled by an axial fitting system, allowing of large scale industrial production, in particular automated mass production, for example using automatic carousels, since the assembly of the various parts of the syringe does not require any relative angular positioning. Moreover, the design of the syringe as per the invention also allows the use of the traditional components of a so-called "triple body" syringe, comprising a cylinder, a piston and a connecting piece.

Moreover the functioning of the syringe as per the invention is absolutely reliable since the displacement of the blocking unit to bring it to its released position is caused only when the piston reaches the end of its path, which means among other advantages that it is possible to inject the whole of the liquid contained in the syringe.

What is claimed is:

1. Medical syringe comprising a tubular body, in which a piston slides, the piston having an opening, a blocking unit blocking said opening before the syringe is used, the blocking unit being arranged to cooperate, when the piston reaches the end of its path, with a counter-piece integral with the tubular body of the syringe, so as to expel said blocking unit out of the opening in such a way that after using the syringe the blocking unit definitively no longer obstructs the opening so that the syringe cannot be re-used, wherein the piston is arranged in such a way as to constitute an rigid inner chamber inside which the blocking unit is housed, the whole being arranged so as to impose a predetermined path on the blocking unit, where the blocking unit has at one of its end a blocking head engaged in the opening and at least one element arranged to prevent its returning to its blocking position, said element resting prior to the injection against the inner wall of said inner chamber, in such a way as to generate a force of friction which is added to the force exerted by the edge of the opening on the blocking head, so that the pressure of the liquid acting on the blocking head during the injection is insufficient to expel the blocking head out of the opening, all the elements of the syringe being designed to be produced by moulding and assembled on an automatic production line by axial fitting.

2. Syringe according to claim 1, wherein the rigid inner chamber comprises an intermediate element and a socket hooked with a notch to the intermediate element, wherein the blocking unit is provided at its rear section with locking elements capable of engaging on an inner shoulder of the intermediate element when the piston reaches the end of its path, thereby placing the locking elements in the active position, and wherein the dimensioning of the assembly components is such that, when mounting the assembly, the head of the blocking unit can engage axially into the intermediate element, the socket can be hooked to the intermediate element after positioning of the blocking unit and the joint device once so assembled can be fixed to the piston by forcing a cylindrical sleeve of the intermediate element in a corresponding bore of the piston.

3. Syringe according to claim 2, wherein the locking elements comprise at least one fin accommodating elastic deformation, whose free end is directed towards the base of the body of the syringe and cooperates with the wall of the inner chamber, said wall being designed so as to allow the free end of the fin to slide against the wall of the inner chamber when the blocking unit moves inside the chamber after having come to a stop against the counter-piece but to then prevent the sliding of the free end of the fin in the opposite direction.

4. Syringe according to claim 3, wherein the inner chamber comprises a first space whose dimensions are chosen in order to maintain the fin folded back along the blocking unit when the blocking head of the blocking unit is blocking the opening and a second space whose dimensions are chosen in order to allow the deployment of the fin when the blocking unit has been moved inside the piston after coming to a stop against the counter-piece.

5. Syringe according to claim 1, wherein the counter-piece comprises at least one element forming a projection in relation to the base of the tubular body of the syringe.

6. Syringe according to claim 2, wherein the counter-piece comprises at least one element forming a projection in relation to the base of the tubular body of the syringe.

7. Syringe according to claim 1, wherein the counter-piece is made up of at least three lugs which project from the base of the tubular body of the syringe, on the periphery of the orifice intended for the injection of the liquid contained in the syringe.

8. Syringe according to claim 1, wherein the counter-piece consists of a crenellated annular projection bordering the orifice intended for the injection of the liquid contained in the syringe.

9. Syringe according to claim 1, wherein the counterpiece consists of a washer with radial arms having, in the centre of the aforesaid washer, a limit acting as a stop for the blocking unit.

10. Seal joint device coupled with the piston of a medical syringe comprising a blocking unit which causes, by coming up against a stop placed in the bottom of the syringe body, when the piston reaches the end of its path, an irreversible deformation of the device so as to exclude any possible reuse of the syringe, said blocking unit being mounted into a guiding assembly coupled to the piston, wherein the assembly itself comprises an intermediate element and a socket hooked with a notch to the intermediate element, wherein the blocking unit is provided at one end with a head provided with locking elements capable of engaging on an inner shoulder of the intermediate element and at the other end with a terminal part which, in active position, closes an opening in the socket, but which is forced back by the stop when the piston reaches the end of its path, thereby placing the locking elements in the active position, and wherein the dimensioning of the assembly components is such that, when mounting the assembly, the head of the blocking unit can engage axially into the intermediate element, the socket can be hooked to the intermediate element after positioning of the blocking unit and the joint device once so assembled can be fixed to the piston by forcing a cylindrical sleeve of the intermediate element in a corresponding bore of the piston.

* * * * *

UNITED STATES PATENT AND TRADEMARK OFFICE
CERTIFICATE OF CORRECTION

PATENT NO.    : 6,083,200
DATED         : July 4, 2000
INVENTOR(S)   : Edgardo Grimm et al.

It is certified that error appears in the above-identified patent and that said Letters Patent is hereby corrected as shown below:

The correct name of the Assignee is SSE System Services Establishment.

Signed and Sealed this

Twentieth Day of November, 2001

Attest:

NICHOLAS P. GODICI
Attesting Officer     Acting Director of the United States Patent and Trademark Office